United States Patent [19]

Finter et al.

[11] Patent Number: 4,657,842

[45] Date of Patent: Apr. 14, 1987

[54] PHOTOSENSITIVE COMPOSITIONS OF MATTER COMPRISING EPOXIDE COMPOUNDS AND FUNCTIONAL ANTHRAQUINONES

[75] Inventors: Jürgen Finter, Freiburg, Fed. Rep. of Germany; Walter Fischer, Reinach; Friedrich Lohse, Oberwil, both of Switzerland

[73] Assignee: Ciba-Geigy Corporation, Ardsley, N.Y.

[21] Appl. No.: 795,029

[22] Filed: Nov. 4, 1985

Related U.S. Application Data

[63] Continuation of Ser. No. 551,767, Nov. 14, 1983, abandoned.

[30] Foreign Application Priority Data

Nov. 25, 1982 [CH] Switzerland .................. 6870/82

[51] Int. Cl.$^4$ ............................................. G03C 1/72
[52] U.S. Cl. ................................... 430/280; 430/270; 430/924; 430/927; 522/48; 522/904
[58] Field of Search ............... 430/280, 270, 924, 927; 522/48, 904

[56] References Cited

U.S. PATENT DOCUMENTS

| | | | |
|---|---|---|---|
| 3,373,140 | 3/1968 | Aftergut | 260/47 |
| 3,822,235 | 7/1974 | Hunter | 204/159.14 X |
| 3,959,547 | 5/1976 | Polichette | 428/209 |
| 4,084,023 | 4/1978 | Dafter | 427/54 |
| 4,097,283 | 6/1978 | Asano | 430/280 |
| 4,105,518 | 8/1978 | McGinniss | 204/159.14 |
| 4,108,803 | 8/1978 | Green | 430/280 |
| 4,177,122 | 12/1979 | Sato | 204/159.18 X |
| 4,262,085 | 4/1981 | Ehrich | 430/417 |
| 4,413,052 | 11/1984 | Green | 204/159.14 X |

FOREIGN PATENT DOCUMENTS

2821500  11/1978  Fed. Rep. of Germany ................. 204/159.14

*Primary Examiner*—John E. Kittle
*Assistant Examiner*—Cynthia Hamilton
*Attorney, Agent, or Firm*—Michael W. Glynn; Irving M. Fishman

[57] ABSTRACT

Photosensitive compositions of matter which are capable of undergoing condensation or addition reactions and may or may not be crosslinkable, and which contain an anthraquinone of the formula I

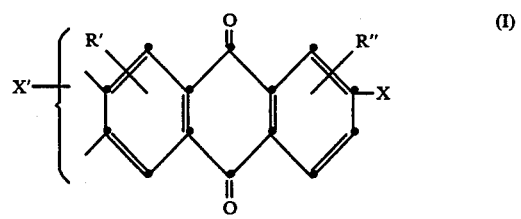

in which X, X', R' and R" are as defined in patent claim 1 and X or X' is, for example, —OH or —NH$_2$, at least one monomeric, oligomeric or polymeric compound which can be reacted with this anthraquinone, for example, if X is —OH, a polymer with terminal glycidyl groups, and, where relevant, a crosslinking agent and/or a salt of a metal of group Ib or VIII of the periodic table, are suitable for image formation by means of electroless metal deposition.

15 Claims, No Drawings

PHOTOSENSITIVE COMPOSITIONS OF MATTER COMPRISING EPOXIDE COMPOUNDS AND FUNCTIONAL ANTHRAQUINONES

This application is a continuation of Ser. No. 551,767, filed Nov. 14, 1983, now abandoned, which claims priority of Swiss Application 6870/82-3, filed Nov. 25, 1982.

The present invention relates to novel photosensitive compositions of matter which are capable of undergoing condensation or addition reactions and may or may not be crosslinkable, reaction products which can be prepared therefrom and processes for their preparation, and the use of the novel photosensitive compositions of matter and reaction products, in particular for image formation.

Electrically conductive coatings and patterns, in particular for printed circuits, can be obtained, inter alia, by producing on non-conductive inorganic or organic substrates zero-valent metal nuclei suitable for electroless metal deposition. This can be effected by the so-called photoformation process, by depositing on the substrate metal salts, in particular salts of non-noble metals, such as copper formate, if appropriate in an acid medium and in the presence of halide ions, and then reducing the salts to zero-valent metal nuclei by irradiation, if necessary in the presence of chemical reducing agents. Photosensitive reducing agents, a second reducing agent and a surfactant are generally used for reducing the metal salts. Photosensitive reducing agents which can be used are, inter alia, anthraquinonedisulfonic acids and salts thereof, if necessary as a mixture with metal activators, such as tin salts. Before deposition of the metal, the substrates must generally be slightly etched or provided with an etchable coating of an adhesion promoter (intramolecular photoreductive method; cf., for example, U.S. Pat. Nos. 3,959,547 and 3,993,802).

According to another process which is already known, a photosensitive layer containing titanium dioxide is produced on the non-conductive substrate, or titanium dioxide is incorporated into the substrate. The substrate containing the titanium dioxide or the layer containing the titanium dioxide must then be etched slightly in order to make the $TiO_2$ particles accessible for further treatment. The slightly etched material is then treated with a solution of the desired metal salt and irradiated (photoelectron method). Finally, zero-valent metal nuclei can also be obtained by first depositing a photosensitive metal salt, such as $SnCl_2$ or iron oxalate, on the non-conductive substrate, forming a latent image or reducing metal ions by irradiation and then producing the zero-valent metal nuclei by reduction of a metal salt, generally a noble metal salt (photo-electrochemical method). The zero-valent metal nuclei thus obtained can then be metallised by electroless metal deposition in a manner which is known per se, and, if appropriate, the conductive image sites can be thickened further by electrolytic deposition of metal.

Novel photosensitive compositions of matter containing anthraquinones have now been found and can be used, or the reaction products which can be prepared therefrom can be used, to produce images, in particular electrically conductive coatings and patterns, in a considerably simpler and more economical manner, it being possible to dispense with the slight etching of the substrate or the use of etchable coatings of an adhesion promoter. The images formed from the novel compositions of matter and their reaction products are also distinguished by an increased release capacity.

The invention thus relates to novel photosensitive compositions of matter which are capable of undergoing condensation or addition reactions and may or may not be crosslinkable, containing (1) an anthraquinone of the formula I

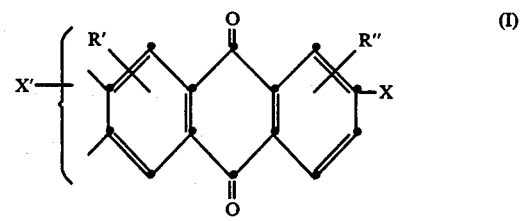

(2) one or more compounds selected from di- to polyglycidyl ethers of phenol and cresol novolaks and compounds of the formulae II to VIII

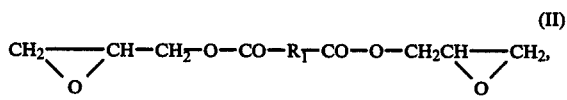

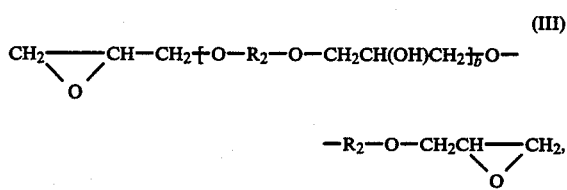

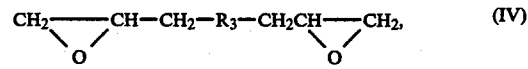

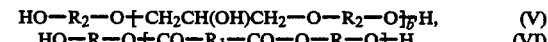
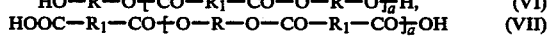
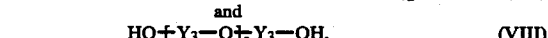
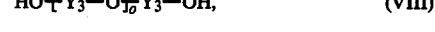

the amount of compounds of the formulae VI, VII and/or VIII being not more than 80 mol %, based on all the reactants mentioned under (2), (3) if appropriate, a crosslinking agent and (4) if appropriate, a salt of a metal of group Ib or VIII of the periodic table, in which R' and R" independently of one another are hydrogen, methyl, halogen or a nitro, phenylsulfonyl or methoxy group, X is —COOH, —COCl, —O—$C_pH_{2p}$—COOH, where $p=1$ to 4, —$NH_2$, —OH, —$CH_2NH_2$, —$CH_2OH$ or

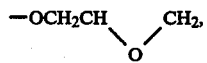

X' is hydrogen or has the same meaning as X, a is a number from 1 to 100, in particular 2 to 50, b is a number from 0 to 150, in particular 0.1 to 150 and especially 2 to 100, b' is a number from 0.1 to 150, in particular 2 to 100, R is —$C_mH_{2m}$—, where $m=2-12$, ($CH_2CH_2O)_rCH_2CH_2$—, where $r=1-40$, in particular 1-20, —$CH(CH_3)CH_2OCH_2CH(CH_3)$—, cyclohexylene, —$CH_2$—$C(CH_3)_2$-$OCOC(CH_3)_2CH_2$—,

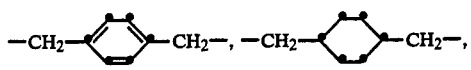

naphthylene, biphenylene, or phenylene which is unsubstituted or substituted by a methyl, methoxy or nitro group, $R_1$ is a direct bond, —$C_mH_{2m}$—, where m=2–12, or cyclohexylene, cyclohexenylene, phenylene or endomethylenecyclohexenylene, each of which can be substituted by a methyl group, $R_2$ is —$C_mH_{2m}$—, where m=2–12, phenylene,

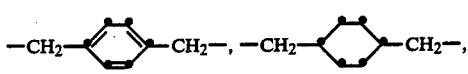

or a group of the formula

Y is hydrogen or methyl, $Y_1$ and $Y_2$ independently of one another are hydrogen, chlorine or bromine, $Y_3$ is —$(CH_2)_2$—, —$CH_2CH(CH_3)$— or —$(CH_2)_4$—, o is a number from 1 to 50 and $R_3$ is

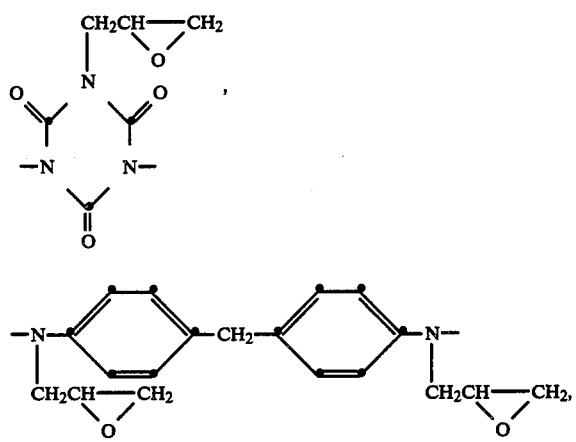

or the radical of ethyleneurea, 1,3-propyleneurea, 5,5-dimethylhydantoin, 2-hydroxyethyl-5,5-dimethylhydantoin or 2-hydroxypropyl-5,5-dimethylhydantoin.

The compositions of matter according to the invention must, as defined, be capable of undergoing condensation or addition reactions. X and X' must therefore be, for example, —COCl, —O—$C_pH_{2p}$—COOH or

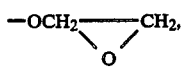

in compounds of the formulae V, VI and/or VIII, or —OH, —$NH_2$, —$CH_2NH_2$, —$CH_2OH$, —COOH or —O—$C_pH_{2p}$—COOH in compounds with glycidyl end groups, and, for example,

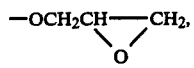

—$NH_2$, —OH, —$CH_2NH_2$ or —$CH_2OH$ in compounds of the formula VII.

The proportion of compounds of the formula I is advantageously between 1 and 60 mol %, preferably 2 to 45 mol %, based on the compounds mentioned under (2).

If a, b or b' is greater than 1, the individual radicals R, $R_1$, $R_2$ and $Y_3$ in the compounds of the formulae III and V to VIII (oligomers or polymers) can have the same or different meanings, and recurring structural elements in such oligomers or polymers can be in random or block arrangement.

Halogen radicals R and/or R' are, in particular, chlorine or bromine atoms. Alkyl groups R and R' can be straight-chain or branched. Examples of suitable alkyl groups R and R' are methyl, ethyl, n-propyl, isopropyl, n-butyl and sec.-butyl. Alkyl groups R and R' are preferably straight-chain and have 1 or 2 C atoms. R and R' are particularly preferably each hydrogen. Alkoxy groups Z can also be straight-chain or branched, but are preferably straight-chain and have 1 or 2 C atoms.

—$C_pH_{2p}$— or —$C_mH_{2m}$— groups X, X', R, $R_1$ and $R_2$ can be straight-chain or branched; p is preferably 1 or 2 and m is preferably 2–10. Examples of such groups are: —$CH_2$—, —$(CH_2)_2$—, —$CH_2CH(CH_3)$—, —$(CH_2)_3$—, —$(CH_2)_4$—, —$(CH_2)_2$—$C(CH_3)_2$—$(CH_2)_2$—, —$(CH_2)_6$—, —$C(CH_3)_2$—, —$CH_2C(CH_3)_2$—$CH_2$—$CH(CH_3)(CH_2)_2$—, —$CH_2CH(CH_3)CH(CH_3)CH_2CH(CH_3)CH_2$—, —$(CH_2)_7$—, —$(CH_2)_8$—, —$(CH_2)_{10}$— and —$(CH_2)_{12}$—.

—$C_mH_{2m}$— groups R and/or $R_2$ are, in particular, radicals of ethylene glycol, butane-1,4-diol, neopentylglycol and hexane-1,6-diol. A —$C_mH_{2m}$— group $R_1$ is derived, in particular, from the radical of succinic acid, adipic acid, pimelic acid, azelaic acid or sebacic acid.

A cyclohexylene radical R is, in particular, the radical of cyclohexane-1,2-diol. Cyclohexylene groups $R_1$ are, in particular, 1,3- and, especially, 1,4-cyclohexylene, which can be substituted by methyl, but are preferably unsubstituted.

A naphthylene or biphenylene radical R or a phenylene radical R which is unsubstituted or substituted by a methyl, methoxy or nitro group is, for example, the radical of 1,4-, 1,6-, 1,8- or 2,6-dihydroxynaphthalene, 2,2'-biphenyl, resorcinol, 2,5-dihydroxyanisole, 1,2-dihydroxy-4-nitrobenzene or 2,5- or 3,4-dihydroxytoluene. R is preferably —$(CH_2)_2$—, —$(CH_2)_4$—, —$(CH_2)_6$—, —$CH_2CH_2OCH_2CH_2$—, —$C(CH_3)_2$—,

or 1,3-phenylene.

A cyclohexenylene, phenylene or endomethylenecyclohexenylene radical $R_1$ which is unsubstituted or substituted by methyl is, for example, the radical derived from methyltetrahydrophthalic acid, endomethylenetetrahydrophthalic acid, tetrahydrophthalic acid, phthalic acid, isophthalic acid or terephthalic acid. $R_1$ is preferably —(CH$_2$)$_m$—, where m=2–10, 1,3- or 1,4-phenylene or 1,3- or 1,4-cyclohexylene.

A phenylene radical R$_2$ is, in particular, 1,3-phenylene.

In a

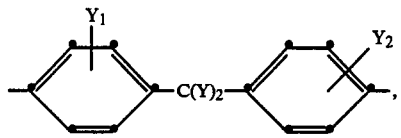

group R$_2$, Y$_1$ and Y$_2$ are preferably each chlorine or bromine bonded in the 2,2'-position. However, those groups in which Y$_1$ and Y$_2$ are hydrogen are particularly preferred. In a —(Y$_3$O)$_o$—Y$_3$ group R$_2$, Y$_3$ is preferably —(CH$_2$)$_2$— or —CH$_2$CH(CH$_3$)— and o is, in particular, 1 to 40, in particular 2–20.

R$_2$ is preferably —C$_m$H$_{2m}$—, where m=2, 4 or 6, or

but in particular a group of the formulae

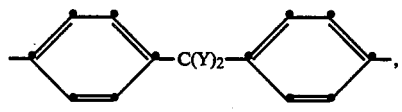

—(CH$_2$CH$_2$O)$_o$—CH$_2$CH$_2$— and/or —[CH$_2$CH(CH$_3$)O]$_o$—CH$_2$CH(CH$_3$)—, where Y is hydrogen and, in particular, methyl and o=1 to 40, in particular 2–20.

R$_3$ is preferably the radical of 5,5-dimethylhydantoin, 2-hydroxyethyl- or 2-hydroxypropyl-5,5-dimethylhydantoin or triglycidyl isocyanurate.

Preferred compositions of matter are those which contain an anthraquinone of the formula I, one or more compounds with glycidyl end groups and/or a compound of the formula V and, if appropriate, a crosslinking agent and/or a metal salt of the type defined, in which R' and R" are hydrogen, X is —CH$_2$NH$_2$, —O—C$_p$H$_{2p}$—COOH or, in particular, —OH, X' is hydrogen, —O—C$_p$H$_{2p}$—COOH which is bonded in the 6-position or, in particular, —OH which is bonded in the 6-position, b' is 0.1 to 100 and b is a number from 1 to 100. —C$_p$H$_{2p}$— is preferably —CH$_2$— or —(CH$_2$)$_2$—. Compounds of the formula I in which R' and R" are hydrogen, X is —CH$_2$NH$_2$ or —OH and X' is hydrogen or —OH which is bonded in the 6-position are preferably used as a mixture with compounds with glycidyl end groups, in particular those of the formulae II to IV, and, if appropriate, compounds of the formula V. If X is —O—C$_p$H$_{2p}$—COOH and X' is hydrogen or —O—C$_p$H$_{2p}$—COOH which is bonded in the 6-position, compounds of the formula V are preferred.

Particularly preferred compositions are those which contain a compound of the formula I in which R' and R" are each hydrogen, X is —CH$_2$NH$_2$ or, in particular, —OH and X' is hydrogen or —OH which is bonded in the 6-position, one or more compounds selected from di- and/or tri-glycidyl ethers of phenol or cresol novolaks, triglycidyl isocyanurate, diglycidyl hexahydrophthalate, N,N'-diglycidyl-5,5-dimethylhydantoin, N-glycidyl-N'-2-hydroxyethylglycidyl- and/or N-glycidyl-N'-2-hydroxypropylglycidyl-5,5-dimethylhydantoin and compounds of the formulae (A), (B), (C) and (D)

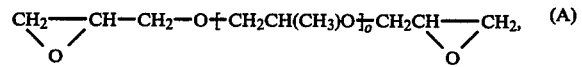  (A)

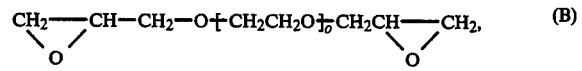  (B)

  (C)

and

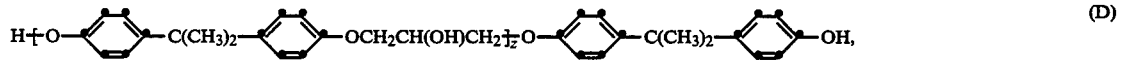  (D)

and, if appropriate, a crosslinking agent and/or a metal salt of the type defined, in which o is 2–40, in particular 2–20, and z is 0.1–13, in particular 2–11.

Especially preferred compositions are those which contain a compound of the formula I in which R' and R" are hydrogen, X is —OH and X' is hydrogen or —OH which is bonded in the 6-position, a compound of the formula (A) or (B) as a mixture with a compound of the formula (C), and, if appropriate, a crosslinking agent and/or a metal salt of the type defined, and those which contain a compound of the formula I in which R' and R" are hydrogen, X is —OH and X' is hydrogen or —OH which is bonded in the 6-position, N,N'-diglycidyl-5,5-dimethylhydantoin, N-glycidyl-N'-2-hydroxyethylglycidyl- and/or N-glycidyl-N'-2-hydroxypropylglycidyl-5,5-dimethylhydantoin, as a mixture with a compound of the formula (C), and, if appropriate, a crosslinking agent and/or a metal salt of the type defined, in which o is 2–20 and z is 2–11.

The invention also relates to the photosensitive reaction products, which may or may not be crosslinked, which can be obtained by reacting a compound of the formula I with one or more compounds selected from di- to poly-glycidyl ethers of phenol and cresol novolaks and compounds of the formulae II to V with suitable functional end groups and, if appropriate, compounds of the formulae VI, VII and/or VIII, in the presence or absence of a crosslinking agent, the proportion of compounds of the formulae VI to VIII being as stated above, and then, if appropriate, at least partly complexing the resulting reaction products with a salt of a metal of group Ib or VIII of the periodic table.

Reaction products which can be obtained by reacting compositions of the above preferred type in a manner which is known per se are preferred.

If several compounds of the type defined under (2) are used, the reaction can also be carried out stepwise by preliminary (poly)addition or (poly)condensation, for example by first reacting the anthraquinone of the formula I with (less than or more than the stoichiometric amount of) a first reaction component of the type defined and then reacting the resulting product with the other reaction component or components in the presence or absence of a crosslinking agent and/or a metal salt of the type defined. On the other hand, it is also possible first to react various compounds of the type defined under (2) with one another and to react the resulting product with the anthraquinone of the formula I in a second stage.

Different linkages of the anthraquinone with the compounds mentioned under (2) and with these latter compounds amongst themselves can be achieved, depending on the type of reaction components and the reaction sequence and depending on which reaction components are used in more than or less than the stoichiometric amount. Thus, for example, it is possible to prepare polymers which contain recurring structural elements of the formula IX, X or XI

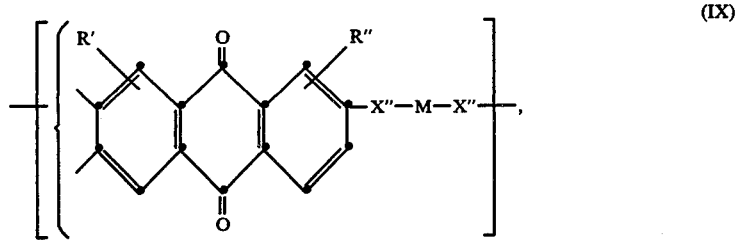

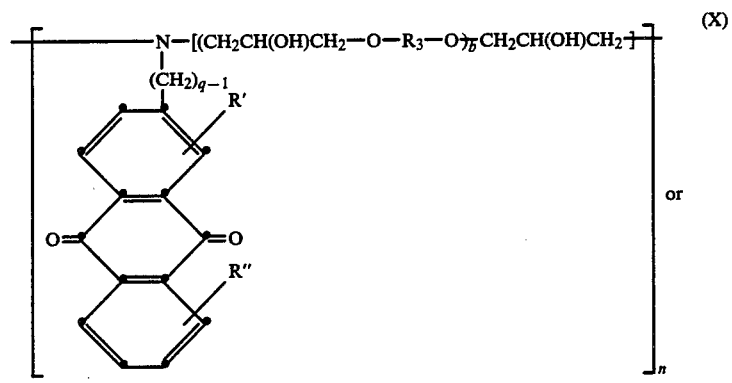

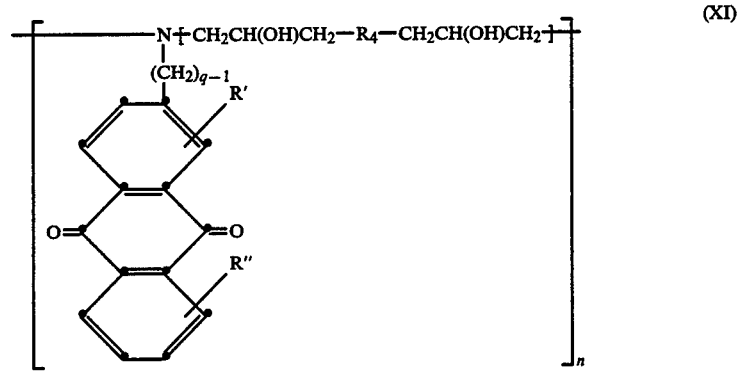

or compounds of the formula XII or XIII

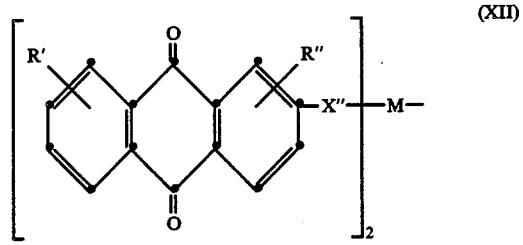

or

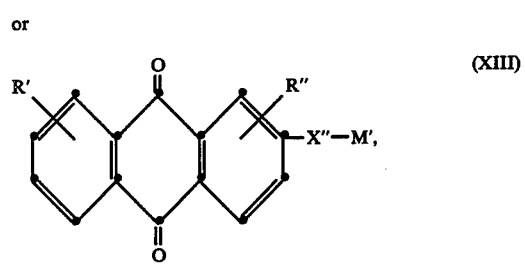

which can be at least partly complexed with metal ions of a metal of group Ib or VIII of the periodic table, in which R' and R" are as defined under formula I, X" is —CO—, —O—$C_pH_{2p}$—CO—, —NH—,

—O—, —CH$_2$NH—,

—CH$_2$O— or —OCH$_2$CH(OH)CH$_2$— and, if X" is —CO— or —O—$C_pH_{2p}$—CO—, the radicals M are identical or different radicals, bonded via —O—, of di- to poly-glycidyl ethers of phenol or cresol novolaks or groupings of the formula IIa, IIIa, Iva or Va

| | |
|---|---|
| —OCH$_2$CH(OH)CH$_2$—O—CO—R$_1$—CO—O—CH$_2$CH(OH)CH$_2$O—, | (IIa) |
| —OCH$_2$CH(OH)CH$_2$—[O—R$_2$—O—CH$_2$CH(OH)CH$_2$]$_b$—O—R$_2$—O—CH$_2$CH(OH)CH$_2$O—, | (IIIa) |
| —OCH$_2$CH(OH)CH$_2$—R$_3$—CH$_2$CH(OH)CH$_2$O— | (IVa) | or

—O—R$_2$—O—[CH$_2$CH(OH)CH$_2$—O—R$_2$—O]$_{b'}$—  (Va)

and, if appropriate, in some cases a grouping of the formula VIa or VIIIa

—O—R—O—[CO—R$_1$—CO—O—R—O]$_a$—  (VIa)

or

—O—[Y$_3$—O]$_o$—Y$_3$—O—  (VIIIa)

or, if X" is —NH—, —O—, —CH$_2$NH— or —CH$_2$O—, the radicals M are identical or different radicals of di- to poly-glycidyl ethers of phenol or cresol novolaks of groupings of the formula IIb, IIIb or Ivb

| | |
|---|---|
| —CH$_2$CH(OH)CH$_2$—O—CO—R$_1$—CO—O—CH$_2$CH(OH)CH$_2$—, | (IIb) |
| —CH$_2$CH(OH)CH$_2$—[O—R$_2$—O—CH$_2$CH(OH)CH$_2$]$_b$— | (IIIb) |
| —CH$_2$CH(OH)CH$_2$—R$_3$—CH$_2$CH(OH)CH$_2$— | (IVb) | and, if appropriate, in some cases a grouping of the formula VIIa

—OC—R$_1$—CO—[O—R—O—CO—R$_1$—CO]$_a$—,  (VIIa)

or, if X" is —OCH$_2$CH(OH)CH$_2$—, the radicals M are identical or different groupings of the formula Va and, if appropriate, in some cases groupings of the formulae VIa, VIIa and/or VIIIa, or, if X" is

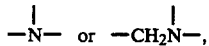

the radicals M are identical or different radicals of di- to poly-glycidyl ethers of phenol or cresol novolaks or groupings of the formula IIb, IIIb or Ivb, and, if X" is —CO— or —O—$C_pH_{2p}$—CO—, the radicals M' are identical or different groupings of the formula IIIc or Vb

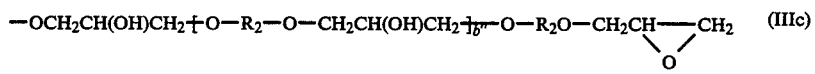

or

—O—R$_2$—O—[CH$_2$CH(OH)CH$_2$—O—R$_2$—O]$_{b''}$H  (Vb)

and, if appropriate, in some cases a grouping of the formula VIb or VIIIb

—O—R—O—[CO—R$_1$—CO—O—R—O]$_{a'}$H  (VIb)

or

—O—[Y$_3$—O]$_{o'}$—Y$_3$—OH ,  (VIIIb)

or, if X" is —NH—, —O—, —CH$_2$NH— or —CH$_2$O—, the radicals M' are identical or different groupings of the formula IIId

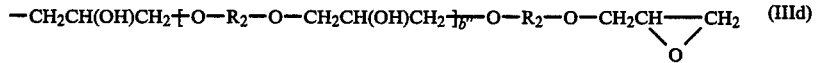

and, if appropriate, in some cases a grouping of the formula VIIb

—OC—R$_1$—CO—[O—R—O—CO—R$_1$—CO]$_{a'}$OH  (VIIb)

or, if X" is —OCH$_2$CH(OH)CH$_2$—, the radicals M' are identical or different groupings of the formula Vb and, if appropriate, in some cases a grouping of the formulae VIb, VIIb and/or VIIIb, or, if X" is

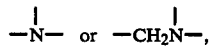

the radicals M' are identical or different groupings of the formula IIId, and a' is a number from 5 to 100, b" is a number from 5 to 150, o' is a number from 5 to 50 and q denotes the number 1 or 2, and a, b, b', R', R", R, p, R$_1$, R$_2$, R$_3$ and Y$_3$ are as defined above.

Linear polymers of the formulae defined above (X" is not

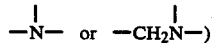

preferably have an average molecular weight of 600 to 500,000, in particular of 2,000 to 150,000, Daltons. The average molecular weight of the polymers can be determined by methods which are known per se, for example by means of osmometry or light scattering.

In certain circumstances, crosslinked products can also be obtained without the addition of crosslinking agents, for example in the reaction of compounds of the formula II, III, IV or V with corresponding anthraquinones of the formula I, in particular those in which X or X' is —$NH_2$ or —$CH_2NH_2$.

Complexing can be carried out before, after or, preferably, during the application of the compositions of matter or of the reaction products obtainable therefrom. Starting polymers containing metal salts of the type defined can also be used in the preparation of polymers according to the invention.

Salts of the metals of the type defined with organic or inorganic acids or mixtures thereof, such as carboxylates, for example formates, acetates, stearates, gluconates and citrates, and halides, nitrates, sulfates and perchlorates, are suitable for the complexing. Examples are: iron-III acetate, citrate, gluconate, nitrate, sulfate and perchlorate; iron-II or iron-III chloride and iron-II oxalate; ruthenium-III chloride; cobalt-II acetate, nitrate or sulfate; cobalt-II chloride or bromide; rhodium-II acetate and rhodium-III chloride; nickel-II acetate, nickel-II bromide and chloride and nickel-II sulfate; palladium-II chloride and iodide and palladium acetate and nitrate; copper-II formate and acetate, copper-I and -II chloride, bromide and iodide and copper-II nitrate or sulfate; and silver acetate, chloride, bromide, nitrate or sulfate. Salts of non-noble metals, in particular iron, cobalt, nickel or copper salts, are preferred. Copper salts, or $Cu^{++}$ ions, are especially preferred. Copper-II carboxylates and copper halides are preferred for the complexing. Copper-II acetate or mixtures of copper-II acetate and copper-II bromide in a molar ratio of 9:1 are particularly used. The degree of complexing is preferably up to 15%, based on the complexable groups of the reaction product or of the starting substances. Examples of complexable groups are OH, NH and secondary amino groups, such as $N(CH_3)_2$ groups.

Depending on the type of functional groups present, examples of crosslinking agents are alcohols, phenols or amines which contain two or more functional groups and di-, tri- or tetra-carboxylic acids or derivatives thereof, such as anhydrides. Examples of suitable polyfunctional compounds are: diols HO—R—OH or HO—$R_2$—OH, dicarboxylic acids HOOC—$R_1$—COOH, oligo-esters of the formula VIII with an average molecular weight of 300–6,000 Daltons, and diamines of the formula $H_2N$—$R_4$—$NH_2$. In these formulae, R, $R_1$ and $R_2$ are as defined above and $R_4$ is —$C_mH_{2m}$—, where m=2–12, cyclohexylene, naphthylene, phenylene which is unsubstituted or substituted by a methyl, methoxy or nitro group, 1,3- or 1,4-xylylene or the radical of 4,4'-diaminodicyclohexylmethane, 4,4'-diaminodiphenylmethane, 4,4'-diaminodiphenylether, 4,4'-diaminodiphenyl sulfone or isophoronediamine. A —$C_mH_{2m}$— radical $R_4$ is preferably —$(CH_2)_2$—, trimethylene, tetramethylene, hexamethylene, —$CH_2CH(CH_3)CH(CH_3)CH_2CH(CH_3)CH_2$— or —$CH_2C(CH_3)_2CH_2CH(CH_3)CH_2CH_2$—.

A naphthylene radical $R_4$ or a phenylene radical $R_4$ which is unsubstituted or substituted by a methyl, methoxy or nitro group is, for example, one of the following radicals: 1,2-, 1,3- or 1,4-phenylene, 4-methoxy-1,3-phenylene, 2-nitro-1,4-phenylene, o- and m-tolylene or 1,5- or 1,8-naphthylene. $R_4$ is preferably —$C_mH_{2m}$—, where m=2–10, 1,3- or 1,4-phenylene or the radical or 4,4'-diaminophenylmethane, 4,4'-diaminodiphenyl ether or isophoronediamine. Other crosslinking agents which can be used are: glycerol, tris(hydroxymethyl)-ethane and -propane, pentaerythritol, diethylenetriamine, triethylenetetramine, succinic anhydride, glutaric anhydride, phthalic anhydride, tetrahydrophthalic and hexahydrophthalic anhydride, trimellitic anhydride, pyromellitic anhydride and benzophenone-tetracarboxylic acid dianhydride. Carboxylic acid anhydrides, such as hexahydrophthalic anhydride or phthalic anhydride, or dihydric or polyhydric alcohols are preferably used for crosslinking compounds containing OH groups and/or glycidyl groups. Crosslinking of compounds containing glycidyl groups with carboxylic acid anhydrides or dihydric alcohols, in particular hexahydrophthalic anhydride or bisphenol A, is preferred.

The condensation or ring-opening addition reactions are advantageously carried out in the presence of an inert organic solvent at temperatures between 90° to 160° C., preferably 100° and 130° C. Examples of suitable solvents are chlorobenzene, dichlorobenzenes, N,N-dialkylamides of aliphatic monocarboxylic acids with 1–3 C atoms in the acid part, such as N,N-dimethylformamide and N,N-dimethylacetamide, ethylene glycol monomethyl and monoethyl ether, N-methylpyrrolidone and ethylene glycol dimethyl or diethyl ether. If appropriate, the reaction can be carried out in the presence of a catalyst, such as N,N-dimethylbenzylamine.

The invention also relates to the 2-aminomethylanthraquinone, which is novel, and the novel anthraquinones of the formula I'

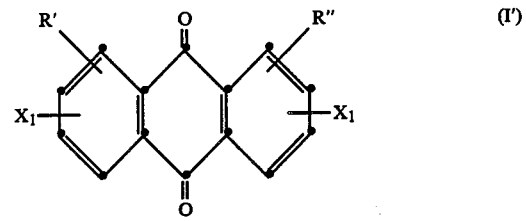

in which R' and R" are as defined under formula I and one of the radicals $X_1$ is hydrogen or

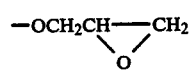

and the other is

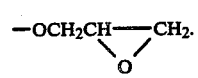

The

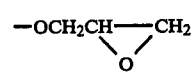

groups are preferably bonded in the 2- or 2- and 6-positions. The compounds of the formula I' can be prepared in a manner which is known per se, by reacting the corresponding hydroxyanthraquinones or dihydroxyanthraquinones with epichlorohydrin.

The remaining compounds of the formula I and the compounds mentioned under (2) are known or they can be prepared by methods which are known per se.

The photosensitive compositions of matter and reaction products according to the invention are used, for example, as sensitisers (redox catalysts) in various oxidation/reduction reactions or as coating materials, for example for corrosion protection of semiconductor photo-diodes or semiconductor lasers. However, they are particularly suitable for image formation by the action of light on various inorganic or organic substrates. Examples of suitable substrates for image formation are glass, metals and metal oxides, such as aluminium, aluminium oxide and copper, ceramics, paper and high molecular weight organic materials. Suitable high molecular weight organic materials are natural and synthetic polymers, for example cellulose materials, such as cellulose acetates, cellulose propionates, cellulose butyrates and cellulose ethers, such as methylcellulose; polymers derived from $\alpha,\beta$-unsaturated acids, such as polyacrylates and polymethacrylates, polyacrylamides and polyacrylonitrile; styrene polymers and copolymers thereof, for example styrene/butadiene copolymers and acrylonitrile/butadiene/styrene copolymers; vinyl and vinylidene polymers and copolymers thereof, such as polyvinyl chloride, polyvinylidene chloride, vinyl chloride/vinylidene chloride copolymers and vinyl chloride/vinyl acetate copolymers; polymers, and derivatives thereof, derived from unsaturated alcohols and amines, such as polyvinyl alcohol, polyvinyl acetate and polyallylmelamine; crosslinked epoxide resins; polyacetals; polyalkylene oxides and polyphenylene oxides; polyamides, polyimides, polyamide/polyimide block copolymers, polysulfones and polyesters; and alkyd resins, for example glycerol/phthalic acid resins and mixtures thereof with melamine/formaldehyde resins, melamine/formaldehyde, urea/formaldehyde and phenol/formaldehyde resins and the like.

The compositions of matter and reaction products according to the invention, in particular the polymers, are used in particular for producing electrically conductive coatings or patterns, in particular printed circuits. For this purpose, the metal ions in the compositions of matter or in the at least partly complexed reaction products are reduced to zero-valent non-conductive metal nuclei (non-conductive visible image points) under the action of light in a manner which is known per se, or, in compositions of matter or reaction products containing no metal salts or metal ions, free radicals are produced, on which electrically conductive metallic coatings or patterns can be produced in the conventional manner by electroless deposition of metals, such as copper, nickel and the like. If desired, these metallic coatings or patterns can be thickened by electrolytic deposition of metal using conventional metal deposition baths. Any suitable light sources can be used for exposing the compositions of matter or reaction products according to the invention, for example Xenon lamps, metal halide lamps and, in particular, high pressure and medium pressure mercury lamps.

EXAMPLE 1

Polymer of 2,6-dihydroxyanthraquinone, bisphenol A diglycidyl ether resin prelengthened with bisphenol A, and polyethylene glycol diglycidyl ether 7.21 g (0.030 mole) of 2,6-dihydroxyanthraquinone, 8.21 g of polyethylene glycol diglycidyl ether having an epoxide equivalent of 5.48 mequivalents/g and 0.077 g of N,N-dimethylbenzylamine are refluxed in 80 ml of ethylene glycol monomethyl ether. After 4 hours, the mixture is allowed to cool to room temperature and 31.76 g of a bisphenol A diglycidyl ether prelengthened with bisphenol A and having an epoxide equivalent of 0.629 mequivalents/g are added. The mixture is then refluxed for 5 hours. The resulting polymer is precipitated in water and dried in vacuo at 80° C. Yield: 43.5 g (92% of theory). Glass transition point=44° C.; average molecular weight (measured by osmometry)=3,500 Daltons. Limiting viscosity $[\eta]=0.134$ dl/g (0.5% by weight at 25° C. in ethylene glycol monomethyl ether).

EXAMPLE 2

Polymer of 2,6-dihydroxyanthraquinone, polypropylene glycol diglycidyl ether and bisphenol A diglycidyl ether resin prelengthened with bisphenol A 3.6 g (0.015 mole) of 2,6-dihydroxyanthraquinone, 7.56 g of a polypropylene glycol diglycidyl ether with an epoxide equivalent of 2.639 mequivalents/g and 0.6 g of N,N-dimethylbenzylamine are refluxed in 50 ml of ethylene glycol monoethyl ether. After 8 hours, the mixture is cooled to room temperature. 23.82 g of a bisphenol A diglycidyl ether prelengthened with bisphenol A and having an epoxide equivalent of 0.629 mequivalents/g are then added and the mixture is refluxed again for 5 hours. The resulting polymer is precipitated from water and dried in vacuo at 80° C. Yield: 26.5 g; epoxide content: 0.085 mequivalents/g; average molecular weight: 4,200 Daltons (determined by osmometry).

EXAMPLE 3

Polymer of 2,6-dihydroxyanthraquinone, hydantoin diglycidyl ether and prelengthened bisphenol A diglycidyl ether resin 0.067 g of N,N-dimethylbenzylamine is added to 7.21 g (0.03 mole) of 2,6-dihydroxyanthraquinone and 6.25 g of a mixture of 70 parts by weight of N,N'-diglycidyl-5,5-dimethylhydantoin and 30 parts by weight of N-glycidyl-N'-hydroxypropyl-glycidyl-5,5-dimethylhydantoin in 80 ml of ethylene glycol monoethyl ether and the mixture is refluxed for 4 hours. It is then cooled to 50° C. 31.67 g of a bisphenol A diglycidyl ether prelengthened with bisphenol A and having an epoxide equivalent of 0.629 mequivalents/g are then added and the mixture is refluxed again for 4 hours. This gives a dark red, viscous solution from which the polymer is obtained by precipitation from water. Yield: 45.1 g; glass transition point=50° C. (determined by differential scanning calorimetry DSC at 20° C./minute). Average molecular weight: 6,000 Daltons (determined by gel permeation chromatography). Epoxide equivalent: 0.04 mequivalent/g.

EXAMPLE 4

A prelengthened product (epoxide equivalent: 0.377 mequivalent/g) is prepared by a process analogous to those described in Examples 1-3 from 0.05 mole of 2,6-dihydroxyanthraquinone and 30.73 g of a polypropylene glycol diglycidyl ether with an epoxide equivalent of 3.25 mequivalents/g. 26.5 g of this product are dissolved in 200 ml of N,N-dimethylformamide with 15.88 g of a bisphenol A diglycidyl ether prelengthened with bisphenol A and having an epoxide equivalent of 0.629 mequivalent/g, 0.771 g of hexahydrophthalic anhydride and 2.16 g of copper-II acetate. Films are produced on polyester foils or on glass fibre-reinforced epoxide sheets with this solution and are crosslinked by drying at 120° C. for 4 hours.

EXAMPLE 5

20.77 g (0.09 mole) of bisphenol A, 27.04 g (0.078 mole) of bisphenol A diglycidyl ether and 0.239 g of N,N-dimethylbenzylamine are heated to an internal temperature of 125° C. in 50 ml of ethylene glycol monomethyl ether under an inert gas, with stirring, and the mixture is stirred for 3 hours. Determination of the phenolic OH groups gives 0.676 mequivalent/g. After cooling to room temperature, 2.96 g of a polyethylene glycol diglycidyl ether with an epoxide equivalent of 5.48 mequivalents/g and 3.78 g of 2,6-anthraquinone diglycidyl ether are added. The reaction mixture is then diluted with 50 ml of ethylene glycol monoethyl ether and heated again to 125° C. for 3 hours. The polymer is isolated by precipitation in water. Yield: 50.2 g (92% of theory); glass transition point=49° C.; average molecular weight: 7,300 Daltons (determined by osmometry).

EXAMPLES 6-8

By a process analogous to those described in Examples 1-3, polyethylene glycol diglycidyl ether with an epoxide equivalent of 5.48 mequivalents/g and a bisphenol A diglycidyl ether prelengthened with bisphenol A and having an epoxide equivalent of 0.629 mequivalent/g are dissolved in a mixture of 6 parts of dioxane and 4 parts of N-methylpyrrolidone, together with 2,6-anthraquinonyldi(oxoacetic acid), and 0.5% by weight of dimethylbenzylamine is added. The solution is stirred at 100° C. for 4 hours. It is then allowed to cool and 2.5% by weight of copper acetate is added. Films are produced on glass sheets by a process analogous to that in Example 9, and are dried at 80° C. for 1 hour and then hardened at 180° for 30 minutes.

The amounts employed and the glass transition point can be seen from the table below.

| Example No. | 2,6-Anthraquinonyl-dioxoacetic acid/g | Polyethylene glycol diglycidyl ether/g | Bisphenol A-bisphenol A diglycidyl ether adduct/g | Glass transition point/°C. |
|---|---|---|---|---|
| 6 | 2.00 | 1.573 | 1.626 | 38 |
| 7 | 2.00 | 1.416 | 1.940 | 52 |
| 8 | 2.00 | 0.885 | 7.701 | 62 |

EXAMPLE 9

To test the photosensitivity, in each case 6 g of the polymers given in the table which follows are dissolved in 20 ml of N,N-dimethylformamide, and 110 mg of copper-II acetate and 10 mg of $CuBr_2$ are added. This solution is applied with a doctor rod to a polyester foil (wet film thickness: 50 m) and, after aerating at room temperature and drying at 70° C. in a circulating air oven, is exposed to a 5 kw high pressure mercury lamp through a mask (21-step sensitivity guide from Stouffer). The image visible after the exposure is thickened in a copper bath having a composition of 12 g of $CuSO_4.5H_2O$/liter, 8 g of HCOH/liter, 15 g of NaOH/liter, 14 g of sodium potassium tartrate/liter, 20 g of ethylenediaminetetraacetic acid/liter and 1 g of octylphenol polyethylene glycol ether/liter at 49° C. The results are shown in the table below.

TABLE

| Polymer according to Example | Exposure time minutes | Exposure temperature °C. | Last step imaged |
|---|---|---|---|
| 1 | 3 | 90 | 3 |
| 2 | 6 | 90 | 4 |
| 3 | 3 | 85 | 2 |
| 4 | 1.5 | 90 | 1 |
| 5* | 3 | 90 | 3 |
| 7 | 3 | 90 | 4 |
| 8 | 3 | 90 | 4 |
| 9 | 6 | 90 | 1 |

*5% by weight of copper-II acetate

Preparation of novel anthraquinones

Example A: Preparation of 2-anthraquinonyl glycidyl ether 112.1 g (0.5 mole) of 2-hydroxyanthraquinone are dissolved in 500 ml of N-methylpyrrolidone, and 12 g (0.5 mole) of sodium hydride are added in portions. When the evolution of gas has ended, 46.37 ml (0.5 mole) of epichlorohydrin are added dropwise at 70° C. and stirring is continued at 70° C. for a further 8 hours. 1.5 liters of water are then added, the mixture is filtered and the filter cake is dried in vacuo. After drying, the product is boiled up again in 1 liter of N,N-dimethylformamide with 10 g of active charcoal and filtered hot. The crystals which precipitate on cooling to 0° C. are separated off by filtration and dried under a high vacuum. 69.45 g (50.57% of theory) of 2-anthraquinonyl glycidyl ether are obtained; melting point: 162°–167° C.

Elemental analysis: calculated: C 72.85, H 4.32, O 22.83%; found: C 73.0, H 4.1, O 22.2%.

Example B: Preparation of 2,6-anthraquinone diglycidyl ether 30.0 g (0.125 mole) of 2,6-dihydroxyanthraquinone are dissolved in 300 ml of N-methylpyrrolidone at 50° C., and 0.25 mole of sodium hydride (as a suspension in oil) is added in portions. When the evolution of gas has ended, 35 g of epichlorohydrin are added and the mixture is stirred at 80° C. for 20 hours. The solution is poured into 5 liters of ice-water and the product which has precipitated is filtered off and dried. 38.3 g (97% of theory) of 2,6-anthraquinone diglycidyl ether are obtained. Recrystallisation from ethylene glycol monomethyl ether with 3% by weight of active charcoal gives 22.1 g of product; melting point: 203° C.

Elemental analysis: calculated: C 68.18, H 4.58, O 27.25%; found: C 68.05, H 4.68, O 27.46%.

Example C: Preparation of 2-aminomethylanthraquinone 10 g (0.039 mole) of 2-chloromethylanthraquinone [prepared according to G. Izoret, Ann. Chim. 7, 180 (1962)] are dissolved in 50 ml of N,N-dimethylformamide (DMF), and 2.53 g (0.039 mole) of sodium azide are added, with stirring. After 1 hour, the temperature is increased to 50° C. and the mixture is stirred at this temperature for 10 hours. 250 ml of water are added and the precipitate is filtered off. 9.5 g (92.3% of theory) of 2-azidomethyl-anthraquinone are obtained; melting point: 130° C. (decomposition).

Analysis for $C_{15}H_9O_2N_3$: calculated: C 68.44, H 3.45, N 15.96%; found: C 67.39, H 3.41, N 15.60%.

9.5 g of 2-azidomethylanthraquinone are dissolved in 100 ml of DMF, 1.0 g of platinum-on-charcoal catalyst (5% by weight of Pt) is added and hydrogenation is carried out with hydrogen for 15 minutes. The catalyst is filtered off, 200 ml of water are added to the filtrate and the mixture is filtered. The red crystals which have precipitated are recrystallised from dioxane. 6.5 g (70.01% of theory) of 2-aminomethylanthraquinone are obtained; melting point: 170°–78° C.

Analysis for $C_{15}H_{11}O_2N$: calculated: C 75.94, H 4.67, N 5.91%; found: C 74.23, H 4.65, N 5.74%.

(D) Preparation of 2,6-anthraquinonyldioxacetic acid 0.125 mole (30 g) of 2,6-dihydroxyanthraquinone is dissolved in 500 ml of N-methylpyrrolidone under an inert gas, with stirring, and 0.25 mole of sodium hydride is added in portions. When the evolution of hydrogen has ended, 0.5 mole (61.2 g) of ethyl chloroacetate are added and the mixture is stirred at 100° C. for 2 hours. 2 liters of water are added, the mixture is rendered neutral with HCl and the product which has precipitated is separated off by filtration. Yield after recrystallisation from ethyl acetate: 31 g=60.1% of theory. Melting point: 175° C.

30 g of the dicarboxylic acid ester are dissolved in oleum, and the solution is added dropwise to water. The product which has precipitated is separated off by filtration. Yield: 19.4 g=(72% of theory) melting point: >300° C. Acid content: 97.15%.

What is claimed is:

1. A photosensitive composition of matter which is capable of undergoing a condensation or addition reaction consisting essentially of
(1) an anthraquinone of the formula I

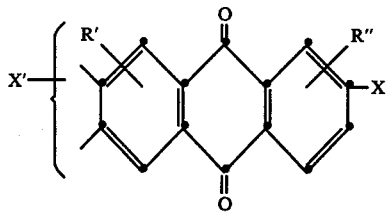

and (2) one or more compounds selected from di- to polyglycidyl ethers of phenol and cresol novolaks and compounds of the formulae II to VIII

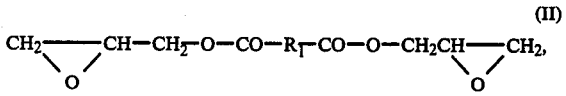

(II)

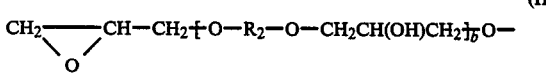

(III)

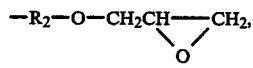

-continued

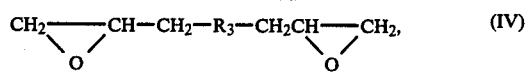

(IV)

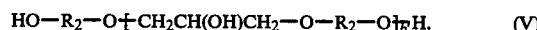 (V)
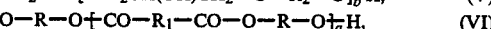 (VI)
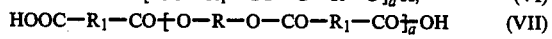 (VII)

and

 (VIII)

the amount of compounds of the formulae VI, VII and/or VIII being not more than 80 mol %, based on all the reactants mentioned under (2), in which R' and R" independently of one another are hydrogen, methyl, halogen or a nitro, phenylsulfonyl or methoxy group, X is —COOH, —COCl, —O—$C_pH_{2p}$—COOH, where p=1 to 4, —NH₂, —OH, —CH₂NH₂, —CH₂OH or

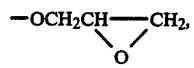

X' is hydrogen or has the same meaning as X, a is a number from 1 to 100, b is a number from 0 to 150, b' is a number from 0.1 to 150, R is —$C_mH_{2m}$—, where m=2–12, (CH₂CH₂O)$_r$—CH₂CH₂—, where r=1–40, —CH(CH₃)CH₂OCH₂CH(CH₃)—, cyclohexylene, —CH₂—C(CH₃)₂—OCOC(CH₃)₂CH₂—,

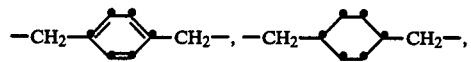

naphthylene, biphenylene, or phenylene which is unsubstituted or substituted by a methyl, methoxy or nitro group, R₁ is a direct bond, —$C_mH_{2m}$—, where m=2–12, or cyclohexylene, cyclohexenylene, phenylene or endomethylenecyclohexenylene, each of which is unsubstituted or substituted by a methyl group, R₂ is —$C_mH_{2m}$—, where m=2–12, phenylene,

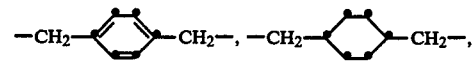

or a group of the formula

Y is hydrogen or methyl, Y₁ and Y₂ independently of one another are hydrogen, chlorine or bromine, Y₃ is —(CH₂)₂—, —CH₂CH(CH₃)— or —(CH₂)₄—, o is a number from 1 to 50 and R₃ is 2-hydroxypropylglycidyl-5,5-dimethylhydantoin and compounds of the formulae (A), (B), (C) and (D)

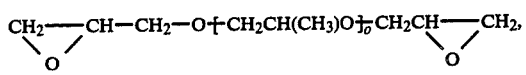  (A)

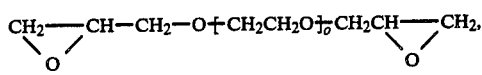  (B)

  (C)

and

  (D)

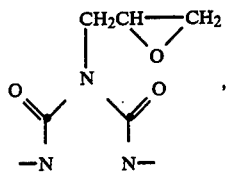

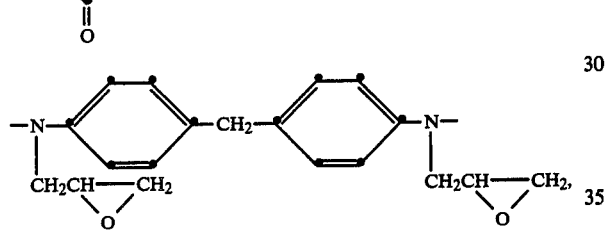

in which o is 2–40 and z is 0.1–13.

4. A composition of matter according to claim 1, containing an anthraquinone of the formula I in which R' and R" are hydrogen, X is —OH and X' is hydrogen or —OH which is bonded in the 6-position, a compound of the formula (A) or (B)

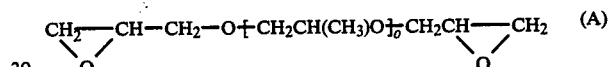  (A)

or

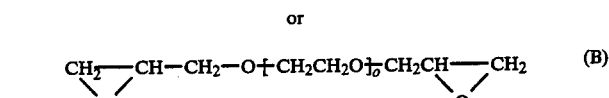  (B)

as a mixture with a compound of the formula (C)

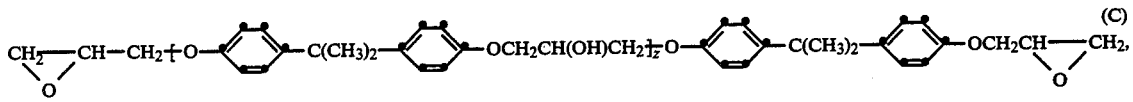  (C)

or the radical of ethyleneurea, 1,3-propyleneurea, 5,5-dimethylhydantoin, 2-hydroxyethyl-5,5-dimethylhydantoin or 2-hydroxypropyl-5,5-dimethylhydantoin.

2. A composition of matter according to claim 1, containing an anthraquinone of the formula I, one or more compounds with glycidyl end groups and/or a compound of the formula V, in which R' and R" are hydrogen, X is —CH₂NH₂, —O—C$_p$H$_{2p}$—COOH or —OH, X' is hydrogen or —O—C$_p$H$_{2p}$—COOH or —OH bonded in the 6-position, b' is a number from 0.1 to 100 and b is a number from 1 to 100.

3. Compositions of matter according to claim 1, containing an anthraquinone of the formula I in which R' and R" are each hydrogen, X is —CH₂NH₂ or —OH and X' is hydrogen or —OH which is bonded in the 6-position, one or more compounds selected from di- and/or tri-glycidyl ethers of phenol or cresol novolaks, triglycidyl isocyanurate, diglycidyl hexahydrophthalate, N,N'-diglycidyl-5,5-dimethylhydantoin, N-glycidyl-N'-2-hydroxyethylglycidyl- and/or N-glycidyl-N'- and in which o is 2–20 and z is 2–11.

5. A composition of matter according to claim 1, containing an anthraquinone of the formula I in which R' and R" are hydrogen, X is —OH and X' is hydrogen or —OH which is bonded in the 6-position, N,N'-diglycidyl-5,5-dimethylhydantoin, N-glycidyl-N'-2-hydroxyethyl and/or N-glycidyl-N'-2-hydroxypropylglycidyl-5,5-dimethylhydantoin, as a mixture with a compound of the formula (C)

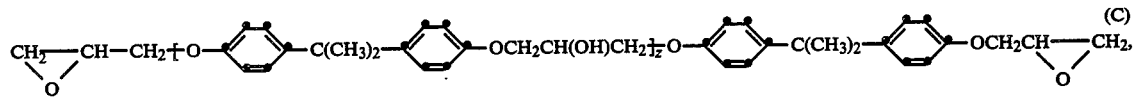  (C)

and in which o is 2–20 and z is 2–11.

6. A photosensitive composition of matter which is capable of undergoing condensation or addition reactions wherein the reactive components thereof consist essentially of components (1) and (2) according to claim 1, and (4) a salt of a metal of group Ib or VIII of the periodic table.

7. A photosensitive composition of matter which is capable of undergoing condensation or addition reactions wherein the reactive components thereof consist essentially of components (1) and (2) according to claim 1, and (3) a crosslinking agent.

8. A composition of matter according to claim 6, containing an iron, cobalt, nickel or copper salt.

9. A composition of matter according to claim 6, containing copper-II acetate or a mixture of copper-II acetate and copper-II bromide.

10. A composition of matter according to claim 7, containing hexahydrophthalic anhydride or bisphenol A as the crosslinking agent.

11. A photosensitive composition of matter which is capable of undergoing condensation or addition reactions wherein the reactive components thereof consist essentially of components (1) and (2) according to claim 1, (3) a crosslinking agent, and (4) a salt of metal of group Ib or VIII of the periodic table.

12. A composition according to claim 1, wherein the acrosslinking agent is hexahydrophthalic anhydride or bisphenol A, and the metal salt is an iron, cobalt, nickel or copper salt.

13. A composition according to claim 1, wherein said metal salt is copper-II acetate or a mixture of copper-II acetate and copper-II bromide.

14. The composition of claim 1 wherein X is selected from (a) COOH, COCl, $OC_pH_{2p}$ COOH wherein p=1-4, $NH_2$, $CH_2NH_2$, $CH_2OH$, and

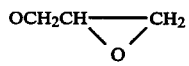

and X' is selected from H and group (a) above.

15. The composition of claim 1 wherein X and X' are both OH.

* * * * *